(12) United States Patent
Lasner

(10) Patent No.: US 6,592,603 B2
(45) Date of Patent: Jul. 15, 2003

(54) MANUALLY ADJUSTABLE SCISSORS OR FORCEPS

(76) Inventor: Michael Lasner, 33 Barker Ave., Suite 5E, White Plains, NY (US) 10601

( * ) Notice: Subject to any disclaimer, the term of this patent is extended or adjusted under 35 U.S.C. 154(b) by 52 days.

(21) Appl. No.: 09/736,463

(22) Filed: Dec. 15, 2000

(65) Prior Publication Data

US 2002/0077649 A1 Jun. 20, 2002

(51) Int. Cl.[7] .......................... A61B 17/28; A61B 17/32
(52) U.S. Cl. .......................... 606/174; 606/207; 30/261
(58) Field of Search .......................... 30/135, 134, 234, 30/261, 266, 235, 254; 606/174, 157, 167, 151, 158, 206, 207, 208, 210

(56) References Cited

U.S. PATENT DOCUMENTS

| | | | | | |
|---|---|---|---|---|---|
| 1,178,684 | A | * | 4/1916 | Shimoda | 30/113.2 |
| 3,003,236 | A | * | 10/1961 | Castelli | 30/234 |
| 3,805,792 | A | * | 4/1974 | Cogley | 606/142 |
| 4,299,030 | A | * | 11/1981 | Vickers | 30/261 |
| 4,392,494 | A | * | 7/1983 | Ashby | 140/121 |
| 4,527,331 | A | * | 7/1985 | Lasner et al. | 30/135 |
| 5,002,554 | A | * | 3/1991 | Korber | 606/174 |
| 5,053,045 | A | * | 10/1991 | Schmidt et al. | 606/155 |
| 5,813,417 | A | * | 9/1998 | Rudolph | 132/200 |

* cited by examiner

*Primary Examiner*—Danny Worrell
(74) *Attorney, Agent, or Firm*—Alfred E. Miller (57) ABSTRACT

A micro-surgical forceps having a handle and integral spring arms that are interconnected at the end of the forceps remote from said blades in a tongue and groove arrangement that allows for operation of the forceps with a minimum of finger pressure. Plastic covers for the handle for securing the forceps blades is a further embodiment of the invention. The forceps are fabricated of a non-heat treatable metal and the gripping platforms are manually adjustable. A scissors having sharpened curved blades that form an arc across one another and are fabricated of non-heated metal that is flexible.

15 Claims, 14 Drawing Sheets

MANUALLY ADJUSTABLE SCISSORS OR FORCEPS

The present invention relates to micro-surgical or non-surgical scissors, which have superimposed blades that are flexible and may be complementary curved. The invention additionally relates to forceps that can be used in microsurgery or other fields in which precise gripping of objects is required. The handle portions of the forceps that control the movement of the blades are resilient bands, or spring arms, so that a minimum of force is required to reliably operate the blades of the forceps and also to apply a pressure release mechanism where excess pressure is released due to the flexibility of the material being used.

BACKGROUND OF THE INVENTION

U.S. Pat. No. 4,527,331 to Lasner et al. shows a suture removing and continuous band scissors having twisted and crossover shanks that are provided with both a cutting and shear blade. That patent is incorporated herein by reference. However, the concept of the above patent is advanced by using sharpened cutting blades that form an arc across one another beyond the optimum shearing angle of heat treated scissors and which results in the scissors always cutting at the points of the blades. The scissors have an intermediate handle portion and rear interconnected metal bands or spring arms, which results in stress relief for the instrument. Furthermore, in accordance with the present invention, the cutting instrument, having rear spring arms that can be operated with a minimum of finger pressure, results a reduction in finger and hand fatigue of the surgeon or other user, while at the same time providing a film holding action.

An alternate embodiment of the invention discloses a continuous band scissors, which is a closed system for increasing energy in the system. The alternate embodiment of the present scissors invention has the advantage of being a closed system whereby energy is trapped within the system and upon continual squeezing goes back to the fulcrum and provides for stronger cutting action of the preferably curved blades.

The prior art forceps that are fabricated of heat-treated metal tend to meet only at the tip. Therefore, when the tips come together and are further pressed resistance is created which will cause the spring to flex and flatten out. In the present invention, on the other hand, the platforms meet initially over the entire surface and are maintained over the entire surface because of the use of spring steel instead of heat treated steel. Furthermore, in the present invention forceps can be reshaped after continual use in order to achieve complete mating of the platforms or in the alternative, the angles of the shanks can be increased or decreased manually resulting in the at rest jaw opening to assume a desired opening or closing distance. This procedure cannot be carried out with heat-treated steel because of the possibility of fracture.

In the present invention the double twist of the forceps is structured with a pivot in-between the two spaced twists, and is also the three point mechanical fixation for optimum stability of operation. Furthermore, the forceps cannot be oversqueezed since the pressure built up in the forceps is relieved out of the back, which is slidingly interconnected. This arrangement is especially valuable with regard to surgery when handling tissue, and can also be used in any field where delicacy of force is required, such as jewelry fabrication.

It is also within the concept of the present forceps invention to place carbon inserts into the platforms or blades so the forceps can be used as a surgical needle holder or to remove metal filings that cannot be successfully gripped by ordinary forceps. The forceps can be used in dentistry, for example, for use with matrix retainers, crown holders as well as with tissue. In addition, the use of carbide inserts in forceps may be successfully utilized as a root canal silver point extraction device for use by endodontists.

SUMMARY OF THE INVENTION

It is a feature of the present invention to provide scissors for micro-surgical or general use having sharpened curved blades and in which the handle portion and rear interconnected spring arms are of different Rockwell C hardness so the instrument required less finger pressure for operation, resulting in reduced finger and hand fatigue for the surgeon.

It is another object of the present invention to provide a scissors of non-heatable steel having sharpened curved or flat blades of resiliently flexible material which form an arc across one another and whereby energy is trapped in a closed system and upon continual squeezing returns to the fulcrum thus providing a stronger cutting action for the blades, thus permitting the tips of the blades to cut thicker material.

It is a feature of the present invention to provide flat interengaging forceps blades, intermediate handle portions for the blades, and spring steel arms which are separate components at the end remote from the forceps blades and which can be assembled and attached to the free ends of the intermediate handle portions to provide a surgical forceps for surgical or other precise usage, which is relatively easy and inexpensive to assemble.

It is another feature of the present invention to provide a part attached to the handle for the forceps constituting a pair of removably interconnected spring bands, preferably of stainless steel, and which are of such a gauge as to be easily and readily pressed toward each other, thus reducing finger and hand fatigue.

A further object of the present invention is to provide forceps having twists of substantially 90° in front of and behind the pivot for the blades whereby the shanks of the forceps can be manually manipulated toward and away from each other to adjust the opening or closing of the blades at rest.

DESCRIPTION OF THE DRAWINGS

In order that the invention may be more clearly understood, it will now be disclosed in greater detail with reference to the accompanying drawings, in which.

DESCRIPTION OF THE PREFERRED EMBODIMENTS

Figure 1:
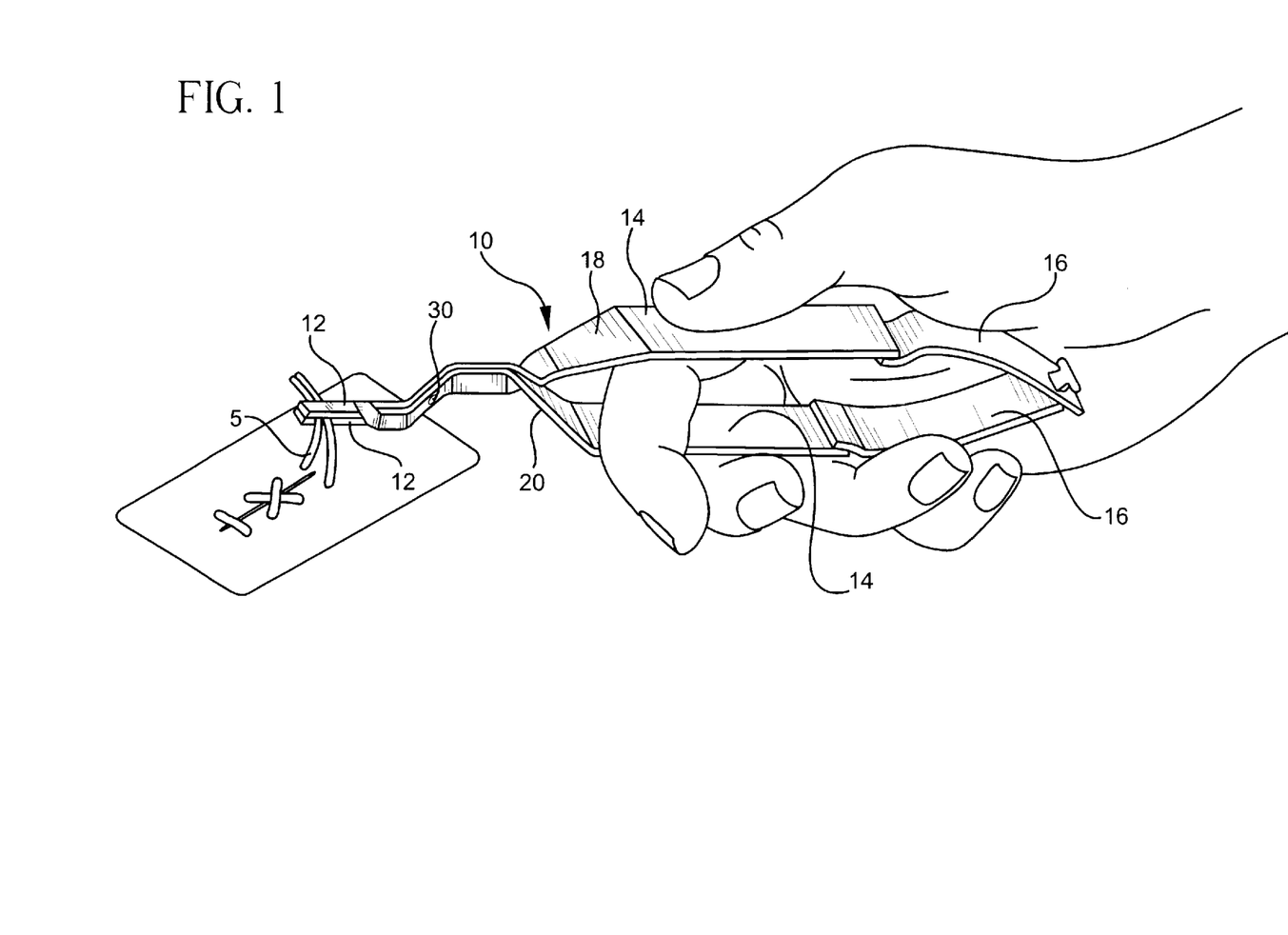
FIG. 1 is a perspective view of the micro-surgical forceps constructed in accordance with the teachings of the present invention shown grasping a suture in its closed at rest position.

Referring to FIGS. 1–6 of the drawings, a micro-surgical instrument which is referred to generally by the reference numeral 10 comprising forceps is shown including flat platforms or blades 12, intermediate handle portions 14 and rear interconnected metal bands or spring arms 16. Shank portions 18 and 20 are each provided with a pair of abutment stops 22 and 24, as well as a first pair of twists 26 and 28, a pivot in the form of a rivet 30, and a second pair of twists 32 and 34. The platforms or flat blades 12 are at the extreme end of the forceps. The rivet 30 is located between the first and second sets of twists. The platforms 12 are rotatable on pivot 30. The forceps shown in FIG. 1 is gripping a suture S, but it should be understood that the forceps can be used effectively when handling tissue and needles, as well.

Figure 4:
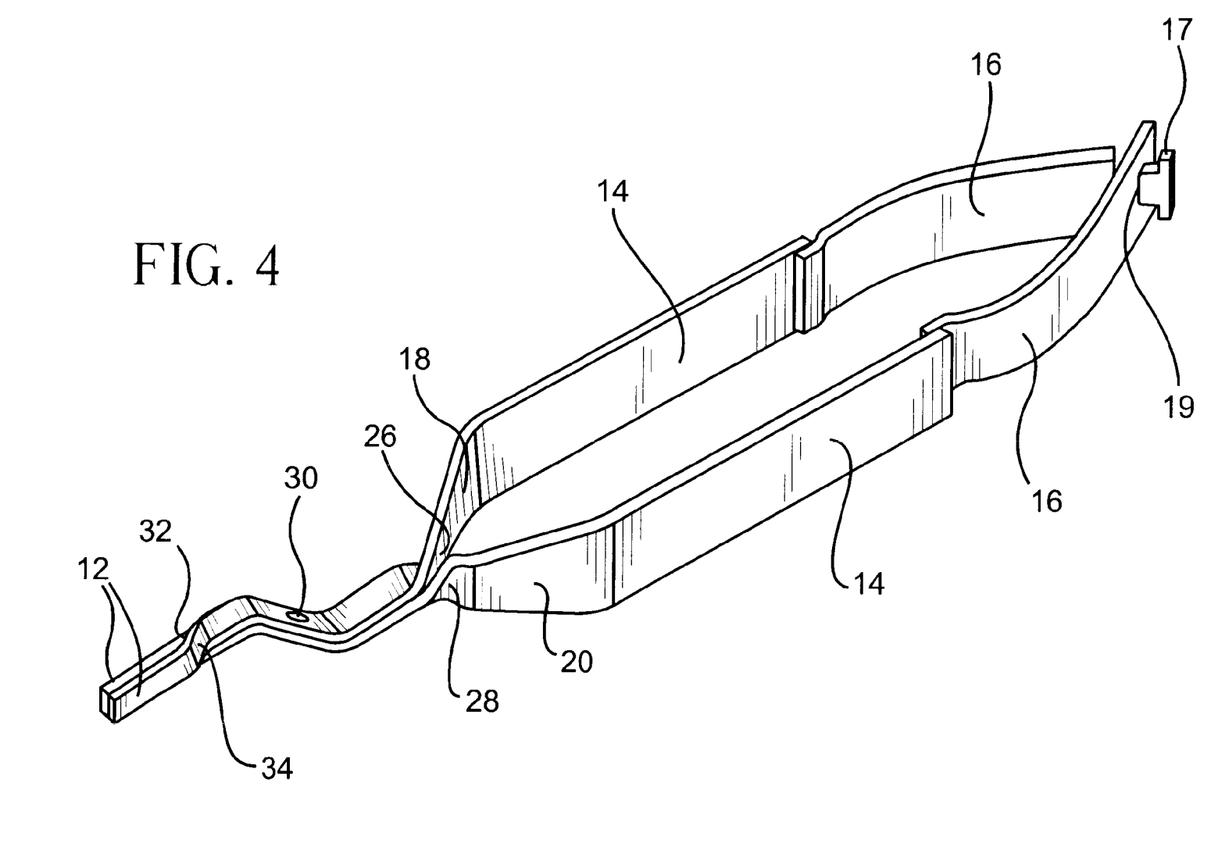
FIG. 4 is a perspective view of the forceps of FIG. 1 showing the micro-surgical forceps in the normally closed position.
Figures 5, 6:
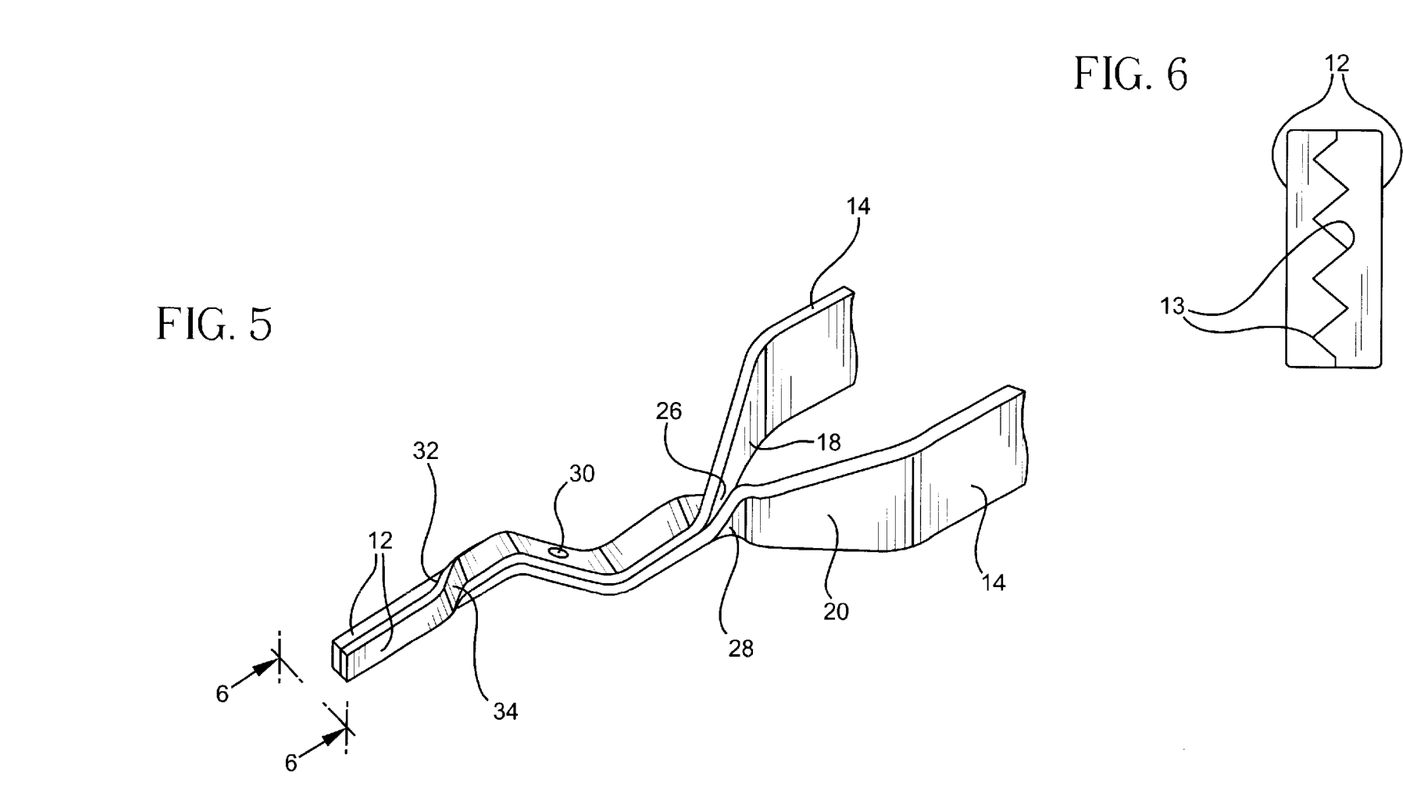
FIG. 5 is a fragmentary enlarged perspective view of the forceps of FIG. 1 showing the micro-surgical forceps shown in FIG. 4.
FIG. 6 is a view taken taken along the lines 6–6 of FIG. 5.

When the handle portions 14 of the forceps are squeezed, the shank portions 18 and 20 are forced toward each other until they firmly abut, as seen in FIGS. 1, 4 and 5, but are prevented from further rotation by means of abutment stops 22 and 24 on each of the shanks.

As seen in FIGS. 1, 4 and 5 the micro-surgical forceps are shown in closed position at rest. However, the handle portions 14 and the spring arms 16 are fabricated of non heat-treatable stainless steel with the handle portions being less resilient than the spring arms. Thus, it is within the scope of the present invention to provide micro-surgical forceps that are constructed of non heat-treatable steel, preferably stainless steel, which can have parts that are produced with different levels of temper, and with varying levels of Rockwell C hardness.

It should be noted that conventional forceps and needle holders would apply all of its closing force to a very delicate needle resulting in a distortion of the needle beyond its elastic limit in many instances. This is because there is no stress relief built into the instrument. When the forceps is used on a very large needle, it is common for the jaws of the instrument to be displaced beyond its elastic limit, rendering the jaws to be permanently splayed causing the instrument to be useless for the purposes intended.

The two basic elements of the forceps which are the handle portion 14 and the metal bands, or spring arms 16 are fabricated separately, but are attached together at 15 by soldering or riveting. The metal bands 16 are interconnected at the end remote from the flat blades 12 by means of a tongue 17 in one band 16 captured but slightly moveable in the opening 19 in the other band 16. The bands 16 are spring steel bands, which are loosely connected at the back end of the forceps. This arrangement considerably reduces the closing tension of the flat blades 12, which is especially useful in delicate micro-surgical procedures where pressure control and tactile sensitivity is important.

Figures 2, 3:
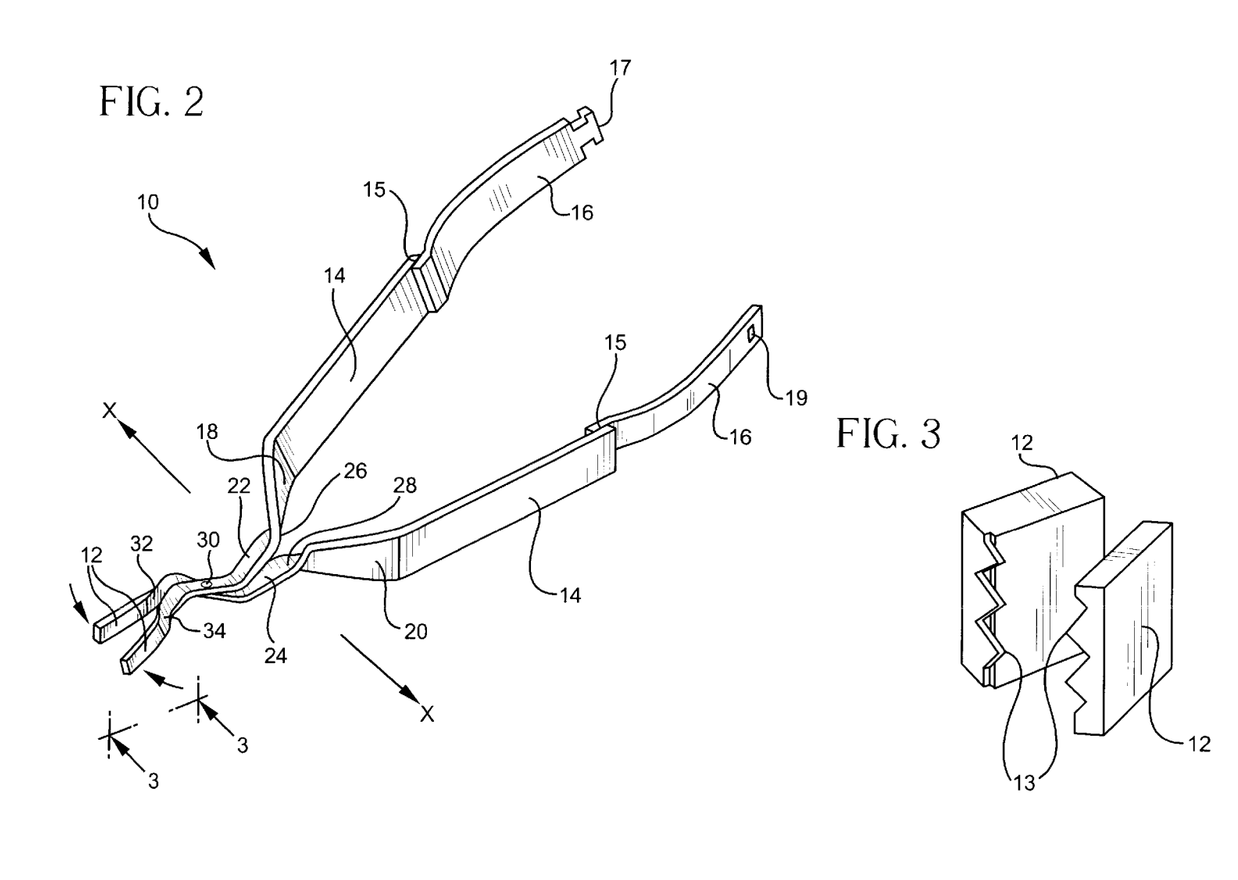
FIG. 2 is a perspective view of the micro-surgical forceps shown in FIG. 1 with rear spring bands separated.
FIG. 3 is a view taken along the lines 3–3 of FIG. 2.

As seen in FIGS. 2 and 3, the user can manually adjust the jaw opening of the gripping platforms of the forceps. By manually moving the shanks 18 and 20 in the directions as shown by the arrows X in FIG. 2 the platforms 12 will engage each other, the angle will be diminished, and the jaws will be closed. On the other hand, by moving the shanks 18 and 20 in opposite directions to the arrow X the angle relationship of the shanks will be increased so that the jaws will open, and that, at rest, the forceps will have its gripping platforms in an open position, as seen in FIGS. 2 and 3, and the extreme forward end of platforms 12 has mating gripping teeth 13 so that objects such as tissue, sutures and needles are firmly gripped when the platforms, or blades, are closed. However, in the case of surgical technologies, the ability to adjust the instrument to be closed at rest allows the surgeon to use the device as a reverse action forceps in that he may open it by reverse pressure whereby access to the tissue can be manipulated. Thus, the surgeon would then have a firm grip on the tissue without having to suffer fatigue by consistently applying pressure, as is the case with prior art forceps.

FIGS. 4, 5 and 6 show the forceps with their gripping platforms 12 in at rest in a closed position with mating gripping teeth interleaved in a closed position. Consequently, the user of the forceps can move the handle portions 14 away from each other against spring pressure in order to grasp an object, such as a suture or tissue. Releasing the handle will cause the object to be held at rest in the jaws of the forceps. When it is desired to release the object, the handle portions are moved away from each other by reverse pressure.

Figure 7:
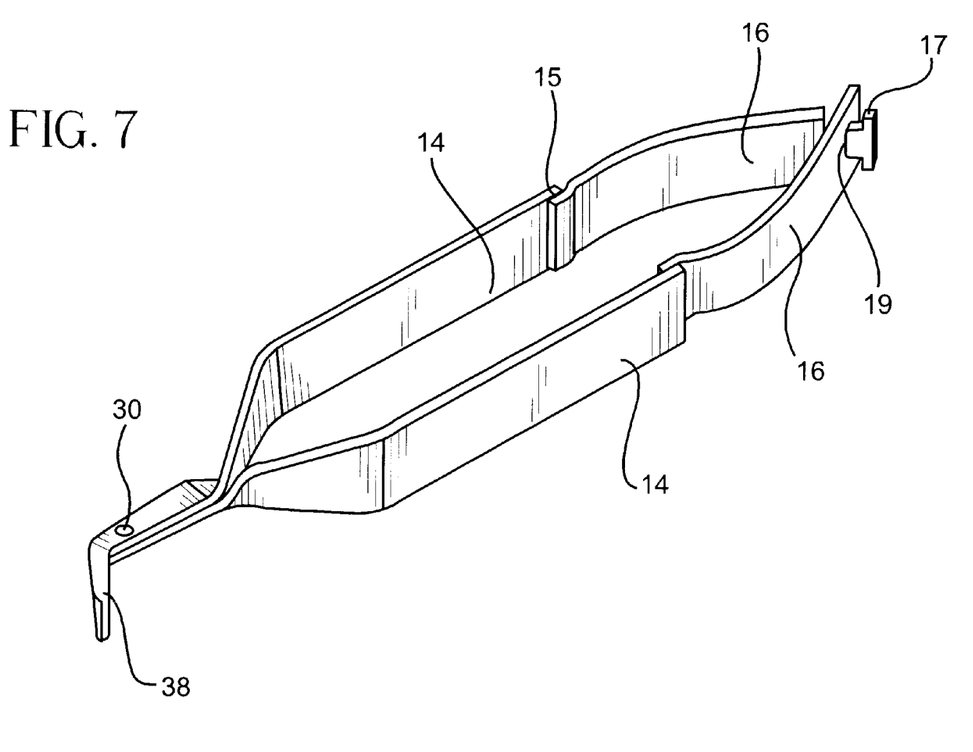
FIGS. 7, 8 and 9 are perspective views of another embodiment of the micro-surgical forceps of the present invention with angular gripping platforms for grouping sutures, tissues and which are also useful in the dental profession.
Figure 8:
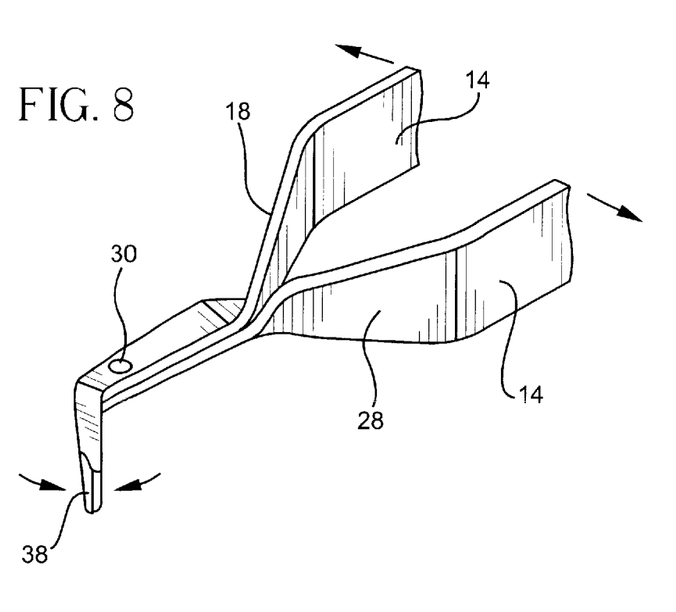
Figure 9:
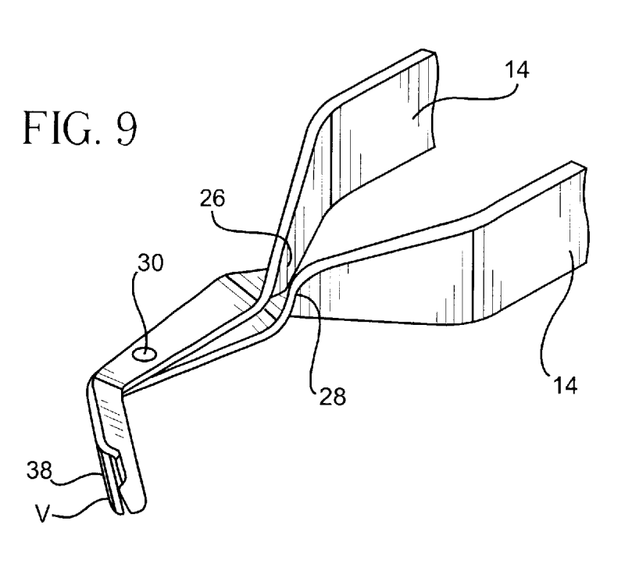

FIGS. 7, 8 and 9 is another embodiment of the of the present invention which has a pronounced angular tip 38 for specialized use, such as handling matrix retainers in dental practice. As seen in FIG. 8 the user can bend the shanks of the yieldable handles 14 in order to open or close the gripping platforms 12. The platforms are shown in desired open condition in FIG. 9.

Figure 10:
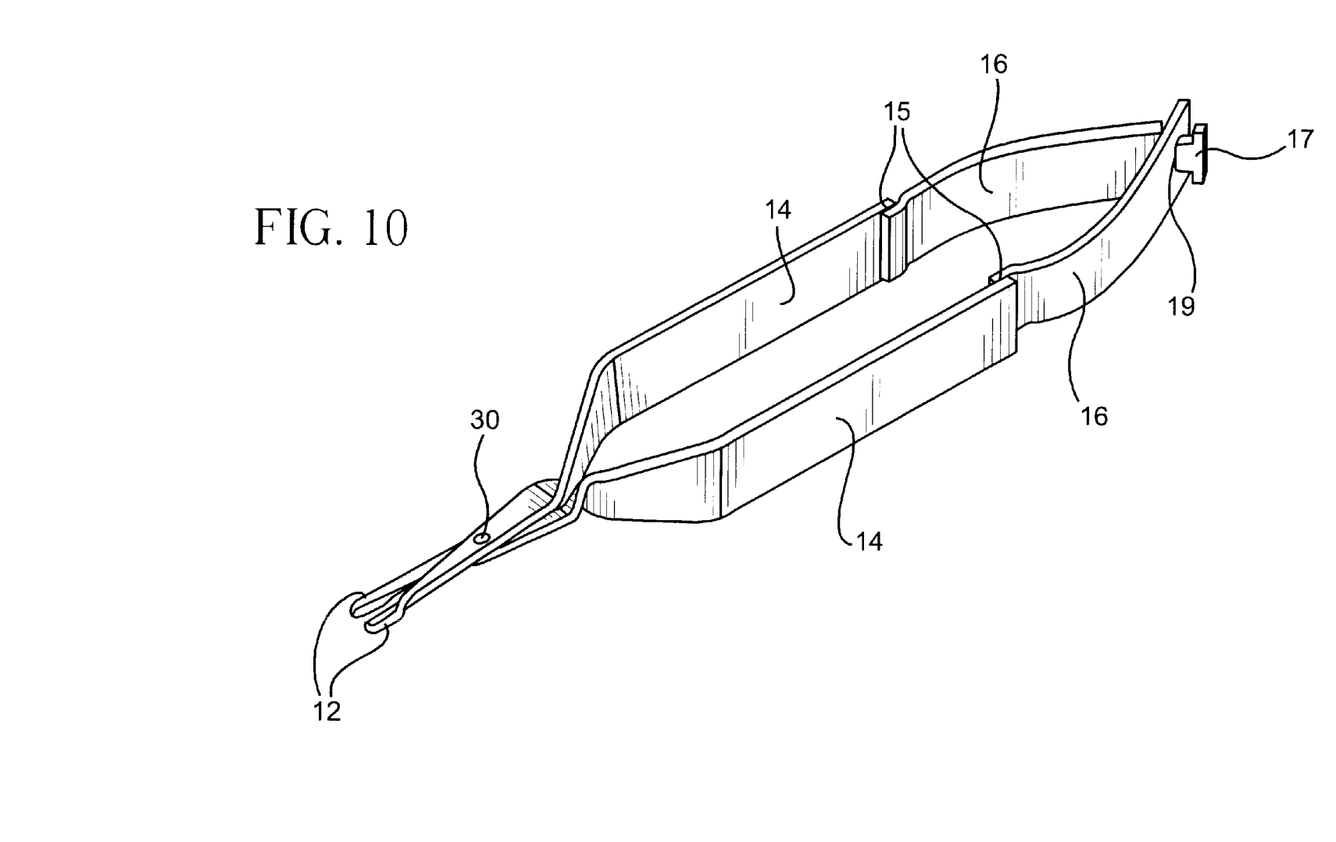
FIGS. 10, 11 and 12 are perspective views of a further embodiment of the micro-surgical forceps of the present invention having straight gripping platforms of the type handling tissue
Figure 11:
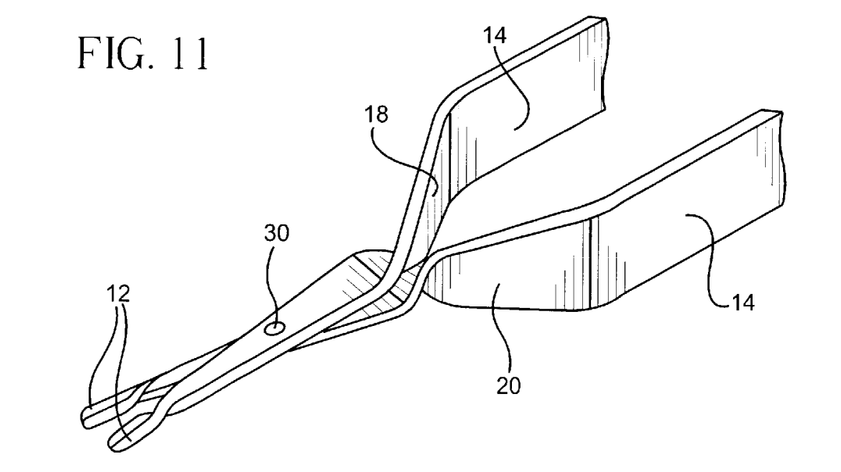
Figure 12:
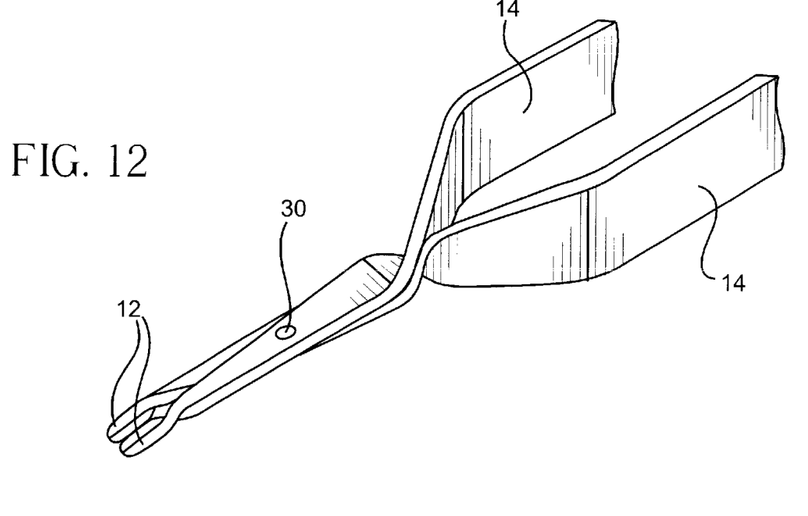

FIGS. 10, 11 and 12 is a further embodiment of the present invention which shows a forceps constructed in accordance with the teachings of the present invention having a twist before and after the rivet 30 and which is particularly useful as a tissue forceps because the resilient properties of the non-heat treatable material used makes the entire instrument flexible to different degrees resulting in stress relief, thus preventing damage to delicate tissues.

Figure 13:
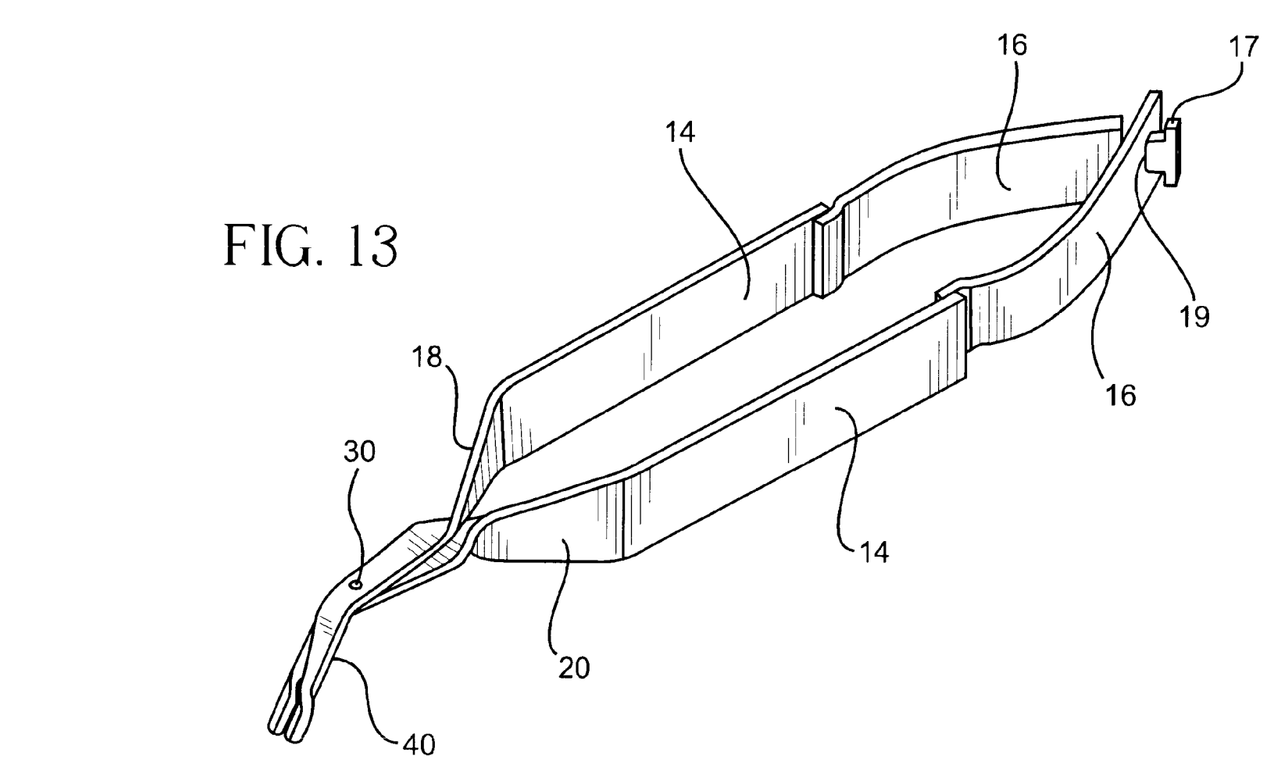
FIGS. 13, 14 and 15 are perspective views of another embodiment of the micro-surgical forceps of the present invention having angular platforms suitable for use, for example in dentistry, as a crown holder.
Figures 14, 15:
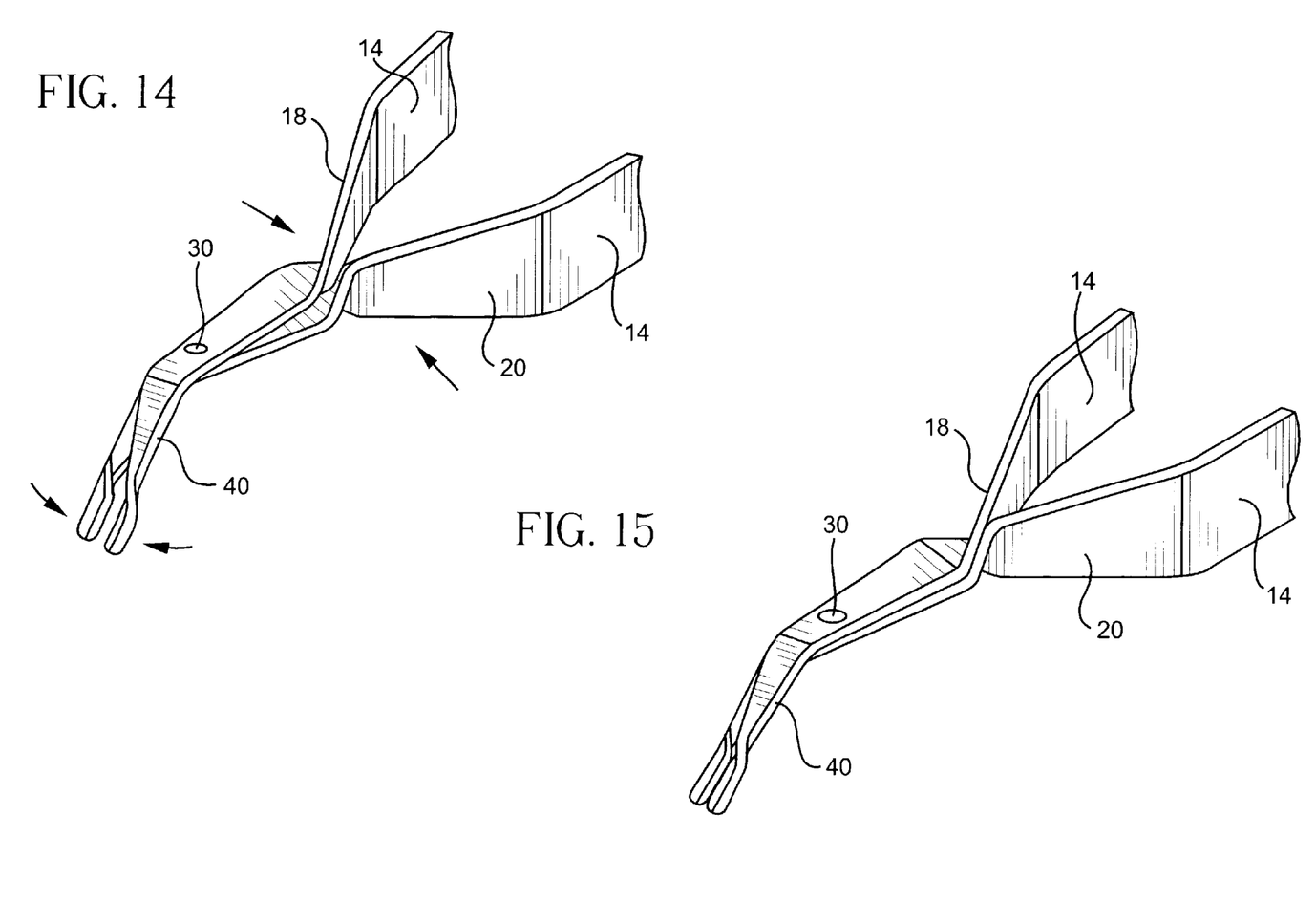

FIGS. 13, 14 and 15 are yet another embodiment of the present invention having angular tip 40 which is less pronounced than the tip of the forceps shown in FIGS. 7–9, but can be manually adjustable as seen in FIG. 14 to either open or close the jaws of the forceps at rest. This device is particularly useful in dentistry as a crown holder.

It should be apparent that the ability of the present forceps to be adjustable is a great improvement not only in surgical and dental techniques, but is also useful for manipulation of nonsurgical materials.

Figure 16:
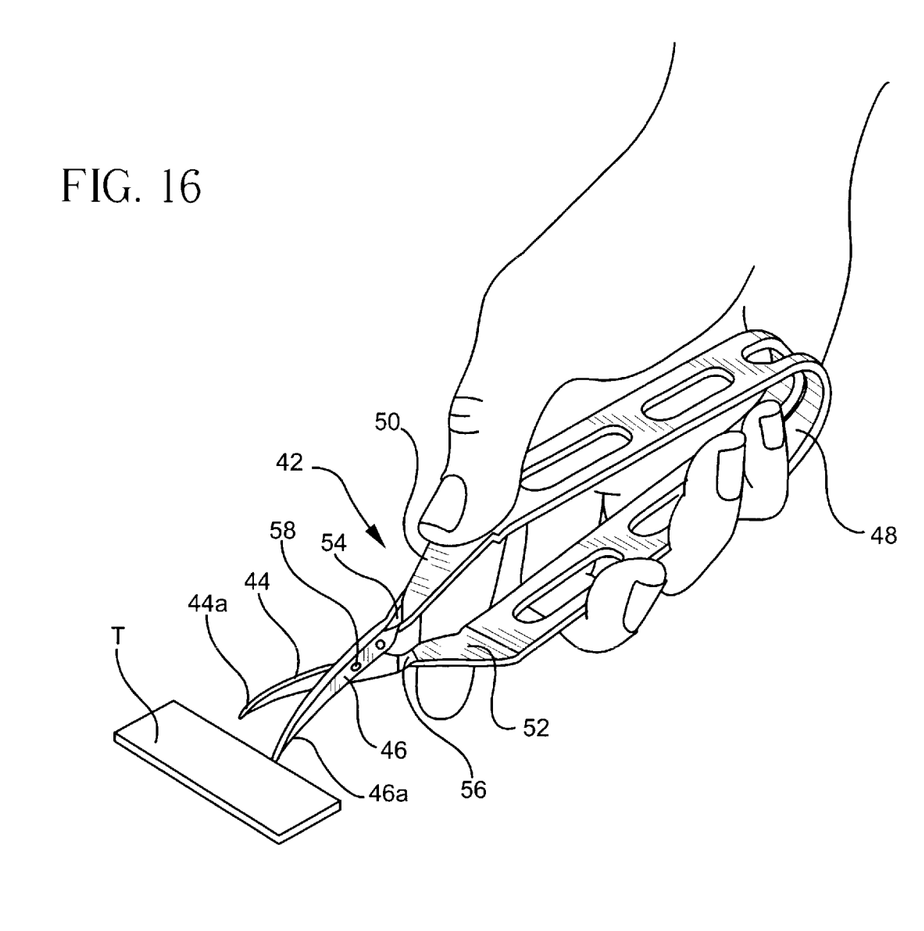
FIG. 16 is a perspective view of an improved closed band scissors, with the curved blades in an open position.
Figure 17:
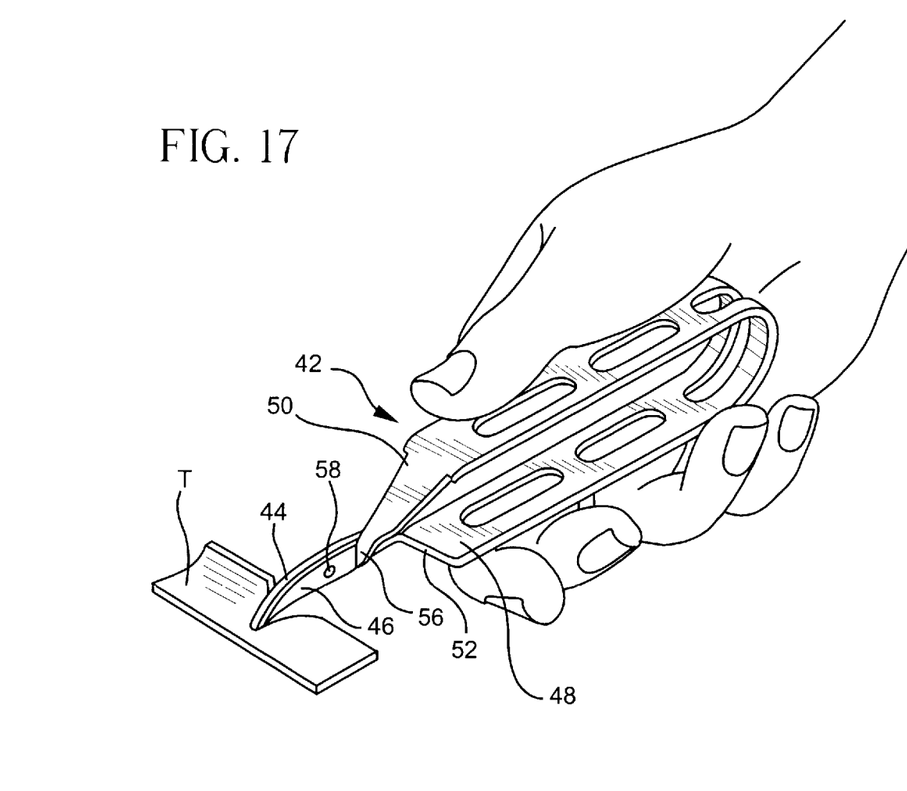
FIG. 17 is a perspective view of the scissors shown in FIG. 7 with the blades in a closed position after cutting material.

Referring to FIGS. 16 and 17, a cutting instrument is shown referred to generally by the reference numeral 42.

The cutting instrument is particularly useful as a micro-surgical scissors having a blade 44 and a shear blade 46. It should be noted that the blades are curved and are fabricated of nonheat treatable steel, such as stainless steel. The blades form an arc across one another thus mandating that the blades will always cut tissue at the point ends 44a and 46a, as seen in FIG. 17. The cutting at the point is accomplished since the blades are flexibly resilient, and at least one of the blades is sharpened.

The cutting instrument 42 is provided with a closed band 48, shanks 50 and 52 as well as twists 54 and 56 so that rear portions of the blades are substantially perpendicular to the planes of the band handle. A rivet 58 holds the blades together.

By squeezing the closed band handle 48 energy is trapped within the closed system and returns to the fulcrum of the scissors upon continual squeezing, and because of the resiliency of the blades a stronger cutting action can be effected, thus permitting the tips of the blades to cut thicker material than is possible with heat treated scissors.

Figure 18:
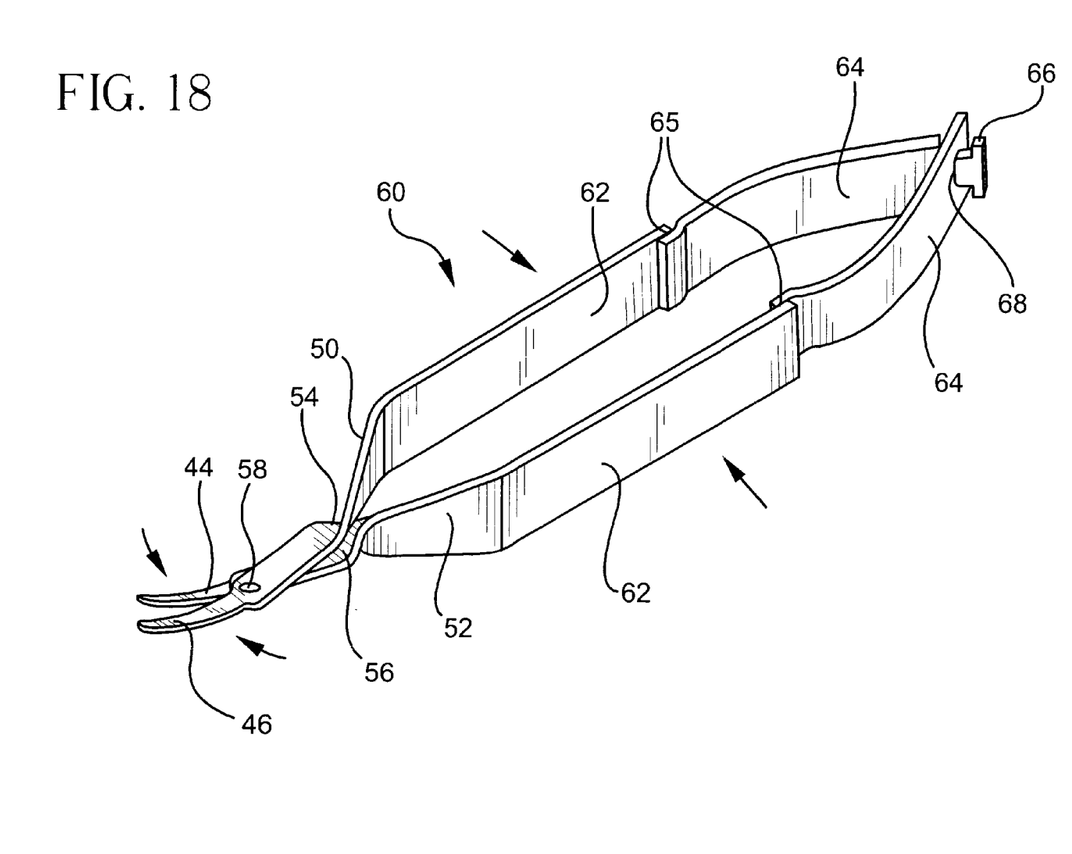
FIG. 18 is a perspective view of another embodiment of the present invention having curved blades but with rear interconnected spring arms affixed to the handle portion at the free ends thereof.
Figure 19:
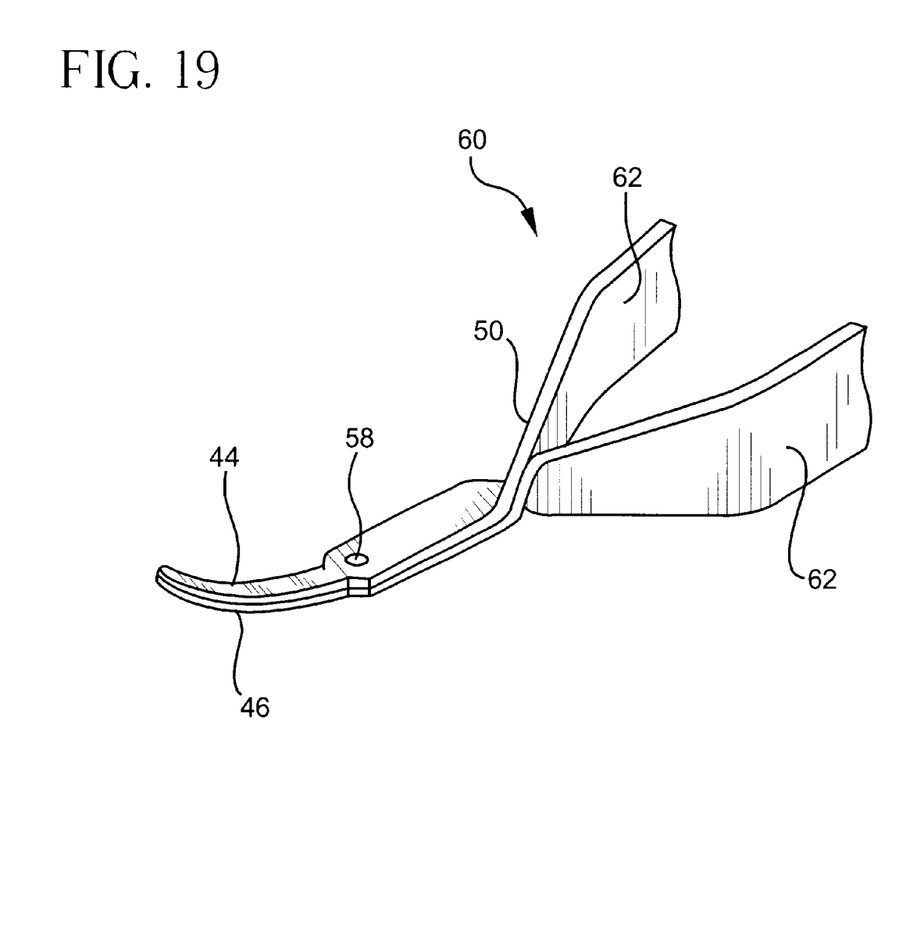
FIG. 19 is an enlarged fragmentary perspective view of the embodiment shown in FIG. 18.

FIGS. 18 and 19 show a cutting instrument, such as a scissors, which is an alternate embodiment of the cutting instrument shown in FIGS. 16 and 17 and referred to generally by the reference numeral 60. The scissors have a handle portion 62, and rear spring metal interconnected bands 64, which are connected to the handle portion at 65 by means of welding 65 or by means of rivets (not shown). The rear metal bands are interconnected at the end remote from the blades 44 and 46 by means of a tongue 66 captured, but slightly movable, within the opening 68 in the adjacent band portion 64. The metal bands are made preferably of non-heat treatable stainless steel that has a lower degree of temper than the handle portion.

The flexibility and light weight of the present scissors when used in the surgical procedures reduces fatigue and allows the surgeon to sever larger tissue, and to manually adjust and reset the blades to their original functioning position after a period of use, since the memory capability of the flexible blades will ensure reliable operation.

While there has been shown and described several embodiments of the present invention, it will be understood that various changes in the form and details of the device illustrated and in its operation may be made by those skilled in the art without departing from the spirit of the invention. It is the intention, therefore, to be limited only as indicated by the scope of the claims appended hereto.

What is claimed is:

1. A scissors fabricated of a non-heat treated yieldable material comprising a single elongated strip bent substantially midway along its length forming a closed band having a finger gripping sections, first and second shanks in spaced apart relationship, said first shank carrying an integral cutting blade at its end remote from said bend, said second shank carrying an integral shear blade at tits end remote from said bend, a twist of substantially 90° in each of said first and second shanks remote from said bend and adjacent to said cutting blade and shear blade to orient said cutting blades in substantially parallel planes, means pivotally connecting said blades for movement toward and away from each other along a cutting plane for contact with material to be cut, said blades being sharpened and forming an arc across one another whereby the blades are flexible and engage one another and are arranged to cut said material at the point ends of said blades, and the closed band builds up energy therein when said finger gripping sections are squeezed whereupon the closing force of the blades is increased.

2. An improved micro-surgical scissors comprising a handle portion, a curved cutting blade and a curved shear blade, each of said blades being fabricated of a non-heat treated bendable steel and having tapered tips, first and second shanks which are disposed in a substantially spaced apart relationship, said first shank carrying said cutting blade, said second shank carrying said shear blade, a twist of substantially 90° in each of said first and second shanks adjacent to the respective blades for movement toward and away from each other by selective movement of said first and second shanks adjacent to said twist, at least a part of each of said shanks extending in a plane substantially perpendicular to the plane of said cutting and shear blades for mutual abutment during the operation of the scissors to prevent pivotal movement of said blades toward each other beyond a pre-determined point, a pair of thin flexible bands attached to the free ends of said handle portion and having a Rockwell hardness that is equal or greater than the Rockwell hardness of said handle portion and cutting blades and each of said bands being provided with interlocking free end parts.

3. A scissors as claimed in claim 2 wherein the means for pivotably moving said cutting blade and shear blade is a rivet, which has a greater resistance to a bending moment than said blades.

4. A micro-surgical scissors as claimed in claim 2 wherein said materials are stainless steel.

5. A scissors as claimed in claim 2 wherein said materials are stainless steel.

6. A scissors as claimed in claim 2 wherein said blades are curved.

7. A scissors as claimed in claim 1 wherein said blades are curved

8. A micro-surgical scissors as claimed in claim 2 wherein said blades are curved 9. An improved forceps for surgical or other uses comprising a handle portion, first and second flat blades of flexible resilient material, first and second shanks on said handle which are disposed in a substantially spaced apart relationship, said first shank having a flat blade at the end remote from said handle portion, a first pair of first and second twists of substantially 90 ° in each of said first and second shanks, a second pair of third and fourth twists of substantially 90° in substantially parallel planes and adjacent to said blades, means between said first and second pair of twists pivotally connecting said blades for movement toward each other along a plane for gripping tissue or other objects, said flat blades being pivotally movable toward each other by selective movement of said handle portion during operation of the forceps to prevent movement of said blades toward each other beyond a pre-determined point, said handle portion being connected at one end to each of said flat blades, and a pair of thin flexible bands each being attached to the other end of said handle portion, and being provided with interlocking free end pens.

10. A scissors as claimed in claim 7 wherein at least part of said handle portion is fabricated of non-heat treatable spring steel.

11. A scissors as claimed in claim 7 wherein said blades are elongated, and further comprising a rivet for affixing said blades together whereby said rivet has a greater resistance to a bending moment than said blades.

12. A scissors as claimed in claim 7 wherein said means pivotally connecting said blades is a rivet whereby said rivet has a greater resistance to a bending moment then said blades.

13. An improved micro-surgical forceps comprising a handle portion, first and second flat blades of flexible resilient material, first and second shanks on said handle which are disposed in a substantially spaced apart relationship, said first shank having a flat blade at the end remote from said bend, said second shank having a flat blade at the end remote from said bend, said second shank having a flat blade at the end remote from said handle portion, a first pair of first and second twists of substantially 90° in each of said first and second shanks, a second pair of third and fourth twists in substantially parallel planes, means pivotably connecting said blades for movement of said blades toward each other beyond a pre-determined point said handle portion being connected at one end to each of said flat blades, a pair of thin flat resilient bands each being attached to the other end of said portion, and being provided with interlocking free end parts.

14. A forceps as claimed in claim 9 wherein said flat resilient bands are attached to the other end if the handle portion by a fixed securement.

15. A method of adjusting the opening or closing of the jaws of a non-heat treated metal material in a forceps as claimed in claim 9 having shanks and a closed handle comprising bending the shanks inwardly toward each other to open said jaws, and bending said shanks outwardly toward each other to close said jaws to self grip an object at rest thereby reducing finger and hand fatigue of the user.

\* \* \* \* \*